United States Patent [19]

Schneider

[11] 4,089,801

[45] May 16, 1978

[54] PROCESS FOR THE PREPARATION OF LIPOSOMES

[75] Inventor: Michel Schneider, Grand Lancy, Switzerland

[73] Assignee: Battelle Memorial Institute, Switzerland

[21] Appl. No.: 648,040

[22] Filed: Jan. 12, 1976

[51] Int. Cl.$^2$ ............................................. B01J 13/02
[52] U.S. Cl. ...................................... 252/316; 424/36; 424/94; 424/179; 424/244; 424/319
[58] Field of Search ........................... 252/316; 424/36

[56] References Cited

U.S. PATENT DOCUMENTS 3,336,155   8/1967   Rowe ................................ 252/316 X

OTHER PUBLICATIONS

Papahadjopoulos et al.: "Cellular Uptake Of Cyclic AMP Captured Within Phospholipid Vesicles and Effect On Cell—Growth Behaviour", Biochim. Biophys. Acta, 363:404–418, (1974).
Papahadjopoulos et al.: "Cochleate Lipid Cylinders:- Formation By Fusion of Unilamellar Lipid Vesicles", Biochim. Biophys. Acta, 394:483–491, (1975).

*Primary Examiner*—Richard D. Lovering
*Attorney, Agent, or Firm*—Robert E. Burns; Emmanuel J. Lobato; Bruce L. Adams

[57] ABSTRACT

Synthetic liposomes, for example containing a biologically active substance, are prepared by dispersing a first aqueous liquid with the aid of ultrasonic vibration in a water-immiscible carrier liquid less dense than water in the presence of a compound of the formula XY where X is a hydrophilic polar group and Y is a hydrophobic non-polar group to form dispersed globules of the first aqueous liquid each bounded by a monomolecular layer of the compound XY; adding this dispersion to a second aqueous liquid to form a two layer system separated and bounded by a monomolecular second layer of the compound XY and then centrifuging the system to force the dispersed globules through the second boundary layer of the compound XY and into the second aqueous liquid.

13 Claims, No Drawings

PROCESS FOR THE PREPARATION OF LIPOSOMES

FIELD OF THE INVENTION

The present invention is concerned with the preparation of synthetic liposomes.

BACKGROUND OF THE INVENTION

Liposomes are fatty or oily globules occurring in cytoplasm. The term "synthetic liposomes" refers to microscopic globules, having a maximum diameter of the order of 10,000 A and preferably having a diameter between 300 and 2,000 A, bounded by a wall formed by at least one bimolecular layer (having a thickness of the order 3,200 A) of a compound of the general formula XY, where X is a hydrophilic polar group and Y is a hydrophobic non-polar group, the globules containing an aqueous liquid, for example an aqueous solution of at least one biologically active substance, and existing generally in the form of a colloidal dispersion in an aqueous medium such as an aqueous saline solution, in particular a 0.9% by weight sodium chloride solution.

The preparation of liposomes provides a method of encapsulation which is most practical and effective for aqueous liquids and which is particularly useful for administration of biologically active substances, particularly medicaments, into living organisms, while avoiding the destruction or inactivation of the substance in the organism, for example by the action of gastric or intestinal juices, before the substances reach the site where they are required to act.

By selection of the compound of formula XY used to form the wall of the liposomes, it is possible to produce liposomes having walls which resist the activity of certain zones in the organism and are only attacked in the presence of particular agents which only exist in the organs where the biologically active substance is to be liberated.

Two processes for the preparation of liposomes are known.

One of these processes consists of placing a lipid in contact with an aqueous liquid which it is wished encapsulate and then warming the heterogeneous mixture thus obtained at a temperature slightly above ambient temperature and then submitting the mixture to vigorous agitation following ultrasonic vibration.

The other process consists of dissolving a compound of formula XY (where X and Y are as defined above), for example a lipid, in a volatile solvent, forming a film of the compound on the walls of a receptacle by evaporating the solvent from the solution thus obtained, introducing in the same receptacle the liquid which is wished to encapsulate in the liposomes, and finally submitting the liquid in the receptacle to the action of ultrasonic vibrations.

The two processes thus require the use of a total volume of the liquid which it is desired to encapsulate very much larger than the volume of that liquid which is finally contained in the liposomes produced by the process. According to these processes, the liposomes are formed in effect in the state of a colloidal dispersion of globules in a liquid phase which comprises the fraction of the liquid to be encapsulated which has not been retained in the interior of the liposomes. The ratio of the volume of encapsulated liquid in the interior of the liposomes to the total volume of the surrounding liquid is in general of the order of 1 to 10%.

In consequence, if the liquid to be encapsulated has a high value, as is the case most generally met when the liquid is a solution of a biologically active substance, it is necessary to recover the fraction of that liquid which has not been encapsulated before using it in further operations to form liposomes. This recovery requires the separation of the liposomes from the liquid, then purification of the liquid itself and, usually, the readjustment of the concentration of the active substance. In practice the separation and purification steps require the use of large volumes of solvents and in consequence the concentration of the liquid containing the active substance has to be adjusted.

The necessity of carrying out the steps of purification and the readjustment of the concentration of the liquid containing the active substance render these two processes difficult to put into practice on an industrial scale.

THE INVENTION

The present invention has as an object an improved process for the preparation of liposomes, using for each preparation only that volume of liquid which is to be encapsulated.

According to the present invention there is provided a process for the preparation of synthetic liposomes, characterised in that a first aqueous liquid is dispersed with the aid of ultrasonic vibration in a carrier liquid which is insoluble in water or only slightly soluble in water and has a density less than that of water, in the presence of at least one compound of the general formula XY, where X represents a hydrophilic polar group and Y represents a hydrophobic non-polar group, so as to form a colloidal dispersion of the first aqueous liquid in the carrier liquid, the dispersed phase being bounded by a monomolecular film of the compound of the general formula XY; this dispersion is combined with a second aqueous liquid to form a heterogeneous two layer system comprising an upper liquid layer formed by the dispersion and a lower liquid layer formed by the second aqueous liquid, the two layers being separated by the monomolecular film of the compound of formula XY; and then the two layer system is centrifuged at an angular velocity sufficient for the dispersed globules of the first aqueous liquid to be forced by gravity through the monomolecular separating film of the compound XY and into the lower layer of the second aqueous liquid.

Thus the process comprises two steps. In the first step a dispersion of globules of the liquid to be encapsulated is formed under the action of ultrasonic vibrations, these globules having colloidal dimensions (i.e. a diameter of the order of 200 to 1,000 A) in a liquid which is either insoluble in water or only slightly soluble in water. These globules are each bounded by a monomolecular film of the compound XY in which the hydrophilic groups X are turned towards the interior of the globules which is occupied by the aqueous liquid and the hydrophobic groups Y are turned towards the outside of the globules which is in contact with a non-aqueous phase. These globules, although they do not, properly speaking, constitute liposomes, since they are not bounded by a bimolecular layer of the compound XY but only by a monomolecular film of that compound, can nevertheless be regarded as prototype liposomes, each of them containing the same volume of the liquid to be encapsulated as the liposomes finally obtained. In the following description, these globules are referred to liposome precursors.

By choosing suitable relative proportions of the aqueous liquid to be encapsulated and the carrier liquid and the compound of formula XY in this first part of the process, it is possible to obtain encapsulation in the liposome precursors of the whole of the liquid to be encapsulated. The process according to the present invention thus avoids the need for recovery, purification or readjustment of the concentration, which, as indicated above, are necessary in the operation of the known processes.

It will also be understood that the process according to the invention allows the encapsulation by the formation of liposomes, of liquids of which only a very small quantity is available, for example quantities of the order of 0.05 to 0.1 milliliter, which would be insufficient for use in the prior art processes described above.

Thus the process according to the invention has applications in fields, such as certain laboratory research or analytical procedures, in which the other processes are inapplicable.

The second step of the process consists of forming the liposomes proper from the liposome precursors. It may be supposed that this formation results from the fact that, in passing through the monomolecular film of the compound XY at the interphase between the upper liquid and the lower liquid, each liposome precursor entrains a part of the interface film between the upper and lower liquids which becomes associated with the monomolecular film of compound XY which surrounds the precursor and thus forms a bimolecular film of the compound XY characteristic of liposomes. The monomolecular film of the compound XY exists at the interface between the upper and lower liquids because of the fact that the hydrophilic groups X are attracted to the aqueous liquid layer while the hydrophobic groups Y remain embedded in the non-aqueous layer.

The compound of formula XY may, for example, comprise a compound in which the hydrophilic group X is one of the following groups: phosphato, carboxylic, sulphato, amino, hydroxyl and choline and in which the hydrophobic group Y is one of the following groups: a saturated or unsaturated aliphatic hydrocarbon group (for example an alkyl or alkylene group), and an aliphatic hydrocarbon group substituted by a least one aromatic or cycloaliphatic group.

Preferably, a phospholipid or a substance closely related to phospholipids is used as a compound of formula XY. In particular the following compounds are useful: lecithin, phosphatidylethanolamine, lysolecithin, lysophosphatidylethanolamine, phosphatidylserine, phosphatidylinositol, sphingomyelin, cardiolipin, phosphatidic acid and the cerebrosides.

It is possible also to use as the compound of formula XY a mixture of at least one phospholipid and at least one other lipid belonging to a category different from the phospholipids. In particular the following compounds may be used: stearylamine, dicetyl phosphate, cholesterol and tocopherol.

The carrier liquid having only a small solubility in water or being insoluble in water is preferably an organic liquid, particularly one of the following compounds: benzene, a halo-benzene or an alkyl benzene, an aliphatic ether, an aliphatic ketone, an aliphatic aldehyde, an aliphatic ester, an aliphatic hydrocarbon or a cycloaliphatic hydrocarbon or a mixture thereof, having a density less than that of water.

The selection of the first aqueous liquid, i.e. the liquid to be encapsulated in the liposomes is limited only by the required utility for the liposomes.

In particular, it is possible to use a solution of at least one biologically active substance, such as an enzyme, or a solution of a medicament such as an antibiotic.

The second aqueous liquid may be pure water or any other aqueous liquid appropriate. For preference the second aqueous liquid is the liquid which is required to be the carrier for the dispersion of the liposomes when they are used, for example an aqueous solution of sodium chloride. In particular an aqueous sodium chloride solution known as physiological serum or physiological saline, having a concentration of 0.15 mole of sodium chloride per liter (0.9% by weight) can be used in order to obtain directly, in the second step of the process, a liposome dispersion in a medium which is injectable in the human body. It is thus a further advantage of the process of the invention as compared with the known processes for the preparation of liposomes, that it is possible to obtain directly a suspension of liposomes in an aqueous medium chosen with regard to the final use of the liposomes.

It is to be understood, however, that it is equally possible to separate the liposomes from the second aqueous liquid, for example if it is wished to remove every trace of the active substance which has not been encapsulated, before the final utilisation of the liposomes. This separation may be easily effected by any appropriate known method, for example by gel chromatography.

The following Examples illustrate the invention.

EXAMPLE 1

An aqueous solution of amyloglucosidase containing 10 mg of amyloglucosidase per milliliter of solution is encapsulated in an aqueous sodium chloride solution (0.15 mole per liter) in the following manner:

Lecithin (54 mg) and the aqueous solution of amyloglucosidase (0.1 ml) are added to dibutyl ether (3 ml) and the heterogeneous mixture thus obtained is subjected to ultrasonic (or near-ultrasonic) vibration (17 kHz frequency: output: 70 Watts) for 2 minutes while maintaining a temperature less than 30° C by means of a cooling bath.

A transparent liquid, apparently homogeneous and having a bluish reflection, is obtained. A layer of this liquid is placed in a centrifuge tube on a layer of 1.5 ml of an aqueous solution of sodium chloride (0.15 mole per liter). There is thus obtained a 2-phase "mixture" comprising a lower layer formed by an aqueous phase (the sodium chloride solution) and an upper layer formed by the organic phase obtained in the first step of the process by ultrasonic vibration of the mixture of dibutyl ether, lecithin and the amylglucosidase solution.

The 2-phase mixture is then centrifuged at 30,000 rev/min for 30 minutes. The upper layer (organic phase) is then removed and the lower layer (aqueous phase) is submitted to a further centrifugation at 30,000 rev/min for 30 minutes. A faintly bluish clear liquid is obtained together with a very small amount of residue comprising non-dispersed lipid (lecithin), which is rejected. The clear liquid comprises a suspension of liposomes (having colloidal dimensions) containing the aqueous amyloglucosidase solution, in a 0.15 M sodium chloride, solution, and also contains a small quantity of non-encapsulated amyloglucosidase.

Depending on how the suspension is to be used, it is possible to use the suspension as formed or after elimination of non-encapsulated amyloglucosidase by gel chromatography (for example on a sepharose (dextran) gel).

EXAMPLE 2

A buffered solution (phosphate buffer 10 mM, pH 7.2) containing 100 mg/ml penicillamine (0.05 ml) is encapsulated in a 0.15 M aqueous solution of sodium chloride, using for the formation of the organic phase subjected to ultrasonic vibration, lecithin (27 mg) and a mixture of dibutyl ether (2.4 ml) and chloroform (0.6 ml). The process is carried out in the same way as in Example 1.

EXAMPLE 3

In a method similar to that of Example 1, an aqueous solution containing 300 mg/ml imipramine (0.1 ml) is encapsulated in a 0.15 M aqueous solution of sodium chloride, using a mixture of lecithin (25 mg) and cholesterol (40 mg) in dibutyl ether (3 ml).

EXAMPLE 4

By a method similar to that of Example 1, an aqueous solution of 150 mg/ml betamethasone disodium phosphate (0.05 ml) is encapsulated in a 0.15 M aqueous solution of sodium chloride using a mixture of lecithin (15 mg) and phosphatidylethanolamine (12 mg) is a mixture of dibutyl ether (2.5 ml) and chloroform (0.5 ml) in the first step.

I claim:

1. A process for the preparation of synthetic liposomes, including the steps of dispersing a first aqueous liquid with the aid of ultrasonic vibration in a carrier liquid which is insoluble in water or only slightly soluble in water and has a density less than that of water, in the presence of at least one compound of the general formula XY, where X represents a hydrophilic polar group and Y represents a hydrophobic non-polar group, selected from the group consisting of phospholipids and lipid-like substances in which the hydrophilic polar group X is selected from phosphato, carboxylic, sulphato, amino, hydroxyl and choline; and in which the non-polar hydrophobic group Y is selected from saturated or unsaturated hydrophobic aliphatic hydrocarbon groups and such aliphatic hydrocarbon groups which are substituted by at least one aromatic or cycloaliphatic group and mixtures of such phospholipids and lipid-like substances, so as to form a colloidal dispersion of the first aqueous liquid in the carrier liquid, the dispersed phase globules, each being bounded by a monomolecular film of the compound of the general formula XY; combining this dispersion with a second aqueous liquid to form a heterogeneous two-layer system comprising an upper liquid layer formed by the dispersion and a lower liquid layer formed by the second aqueous liquid, the two layers being separated by the monomolecular film of the compound of formula XY; and then centrifuging the two-layer system at an angular velocity sufficient for the dispersed globules of the first aqueous liquid to be forced by gravity through the monomolecular separating film of the compound XY and into the lower layer of the second aqueous liquid.

2. The process of claim 1 wherein the compound of the general formula XY is a phospholipid.

3. The process of claim 2 wherein the phospholipid is selected from the group consisting of lecithin, phosphatidylethanolamine, lysolecithin, lysophosphatidylethanolamine, phosphatidylserine, phosphatidylinositol, sphingomyelin, cardiolipin, phosphatidic acid and the cerebrosides.

4. The process of claim 1 wherein the compound of the general formula XY comprises at least one phospholipid and at least one other lipid belonging to a category of lipids other than the phospholipids.

5. The process of claim 4 wherein the said other lipid is selected from the group consisting of stearylamine, dicetyl phosphate, cholesterol and tocopherol.

6. The process of claim 1 wherein the said carrier liquid is an organic liquid.

7. The process of claim 6 wherein the said organic liquid is selected from the group consisting of benzene, halo-benzenes, alkyl benzenes, aliphatic ethers, aliphatic ketones, aliphatic aldehydes, aliphatic esters, aliphatic hydrocarbons and cycloaliphatic hydrocarbons and mixtures thereof.

8. The process of claim 1 wherein said first aqueous liquid is an aqueous solution of at least one biologically active substance.

9. The process of claim 8 wherein the said active substance is an enzyme.

10. The process of claim 8 wherein the said active substance is an antibiotic.

11. The process of claim 1 wherein the second aqueous liquid is an aqueous solution of sodium chloride.

12. The process of claim 11 wherein the said solution of sodium chloride contains 0.15 moles of sodium chloride per liter.

13. A process for the preparation of synthetic liposomes, comprising the steps of (a) dispersing a first aqueous liquid consisting of a solution of a biologically active substance, with the aid of ultrasonic vibration in a carrier liquid which is insoluble in water or only slightly soluble in water and has a density less than that of water, in the presence of at least one interface compound selected from the group consisting of lecithin, phosphatidylethanolamine, lysolecithin, lysophosphatidylethanolamine, phosphatidylserine, phosphatidylinositol, sphingomyelin, cardiolipin, phosphatidic acid and the cerebrosides or a mixture thereof with at least one lipid selected from the group consisting of stearylamine, dicetyl phosphate, cholesterol and tocopherol, so as to form a colloidal dispersion of the first aqueous liquid in the carrier liquid, the dispersed phase globules each being bounded by a monomolecular film of the said interface compound; (b) combining this dispersion with a second aqueous liquid to form a heterogeneous two-layer system comprising an upper liquid layer formed by the dispersion and a lower liquid layer formed by the second aqueous liquid, the two layers being separated by the monomolecular film of the said interface compound; and (c) centrifuging the two layer system at an angular velocity of about 30,000 rev/min to force the dispersed globules of the first aqueous liquid by gravity through the monomolecular separating film of the interface compound and into the lower layer of the second aqueous liquid.

* * * * *

Dedication 4,089,801.—*Michel Schneider*, Grand Lancy, Switzerland. PROCESS FOR THE PREPARATION OF LIPOSOMES. Patent dated May 16, 1978. Dedication filed Mar. 26, 1984, by the assignee, *Battelle Memorial Institute*.

Hereby dedicates to the People of the United States the entire remaining term of said patent.

[*Official Gazette May 22, 1984.*]